United States Patent [19]

Yukinaga et al.

[11] 4,111,680
[45] Sep. 5, 1978

[54] HERBICIDAL COMPOSITIONS CONTAINING 3-ISOXAZOLYLUREA DERIVATIVES

[75] Inventors: Hisajiro Yukinaga, Kusatsu; Shinzaburo Sumimoto, Osaka; Ichiro Ishizuka, Higashinose; Jitsuo Sugita, Ikeda, all of Japan

[73] Assignee: Shionogi & Co., Ltd., Osaka, Japan

[21] Appl. No.: 836,238

[22] Filed: Sep. 23, 1977

Related U.S. Application Data

[60] Division of Ser. No. 667,033, Mar. 15, 1976, Pat. No. 4,062,861, which is a continuation of Ser. No. 491,491, Jul. 23, 1974, abandoned.

[30] Foreign Application Priority Data

Jul. 27, 1973 [JP] Japan .................................. 48-85339

[51] Int. Cl.$^2$ ............................................. A01N 9/22
[52] U.S. Cl. ............................................................. 71/88
[58] Field of Search ............................................. 71/88

[56] References Cited

U.S. PATENT DOCUMENTS 3,547,940  12/1970  Brantley .............................. 71/88 X
4,060,402  11/1977  Tomita et al. ....................... 71/88 X

*Primary Examiner*—Catherine L. Mills
*Attorney, Agent, or Firm*—Wenderoth, Lind & Ponack

[57] ABSTRACT

Isoxazole derivatives represented by the formula:

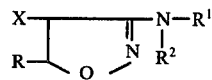

wherein R represents hydrogen, alkyl group, or aryl group, $R^1$ represents hydrogen, or alkyl group, $R^2$ represents acyl group, a

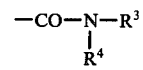

group

[$R^3$ and $R^4$ each represent hydrogen, alkyl group, alkenyl group, alkynyl group, aralkyl group, aryl group, alkoxy group, or alkylthio group; or optionally $R^3$ and $R^4$ are combined with each other directly or indirectly including another hetero atom (nitrogen, oxygen, or sulfur) to form a nitrogen-containing ring], or a —CO—Y—$R^5$ group

[$R^5$ represents alkyl group, alkenyl group, alkynyl group, aralkyl group, or aryl group, and Y represents oxygen, or sulfur], and X represents hydrogen, alkyl group, or halogen, or R and X are optionally combined each other to form an alkylene group, said alkyl group, aralkyl group, and aryl group each being optionally substituted with one or more members selected from halogen, alkyl group, alkoxy group, nitro group, and hydroxy group, are prepared by 11 routes. The isoxazole derivatives are useful as herbicides.

13 Claims, No Drawings

HERBICIDAL COMPOSITIONS CONTAINING 3-ISOXAZOLYLUREA DERIVATIVES

This is a division of application Ser. No. 667,033, filed Mar. 15, 1976 now U.S. Pat. No. 4,062,861 which is a continuation of application Ser. No. 491,491 filed July 23, 1974 now abandoned.

The present invention relates to isoxazole derivatives and herbicides containing them. More particularly, this invention relates to isoxazole derivatives represented by the formula:

wherein R represents hydrogen, alkyl group ($C_1$ to $C_6$), or aryl group ($C_6$ to $C_{12}$), $R^1$ represents hydrogen, or alkyl group ($C_1$ to $C_6$), $R^2$ represents acyl group ($C_1$ to $C_{10}$),

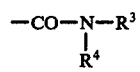

group
[$R^3$ and $R^4$ each represent hydrogen, alkyl group ($C_1$ to $C_6$), alkenyl group ($C_2$ to $C_7$), alkynyl group ($C_2$ to $C_7$), aralkyl group ($C_7$ to $C_{14}$), aryl group ($C_6$ to $C_{12}$), alkoxy group ($C_1$ to $C_6$), or alkylthio group ($C_1$ to $C_6$); or optionally $R^3$ and $R^4$ are combined with each other directly or indirectly including another hetero atom (nitrogen, oxygen, or sulfur) to form a nitrogen-containing ring], or a —CO—Y—$R^5$ group
[$R^5$ represents alkyl group ($C_1$ to $C_6$), alkenyl group ($C_2$ to $C_7$), alkynyl group ($C_2$ to $C_7$), aralkyl group ($C_7$ to $C_{14}$), or aryl group ($C_6$ to $C_{10}$), and Y represents oxygen, or sulfur], and X represents hydrogen, alkyl group ($C_1$ to $C_6$), or halogen, or R and X are optionally combined with each other to form an alkylene group ($C_4$ to $C_6$), said alkyl group, aralkyl group, and aryl group each being optionally substituted with one or more members selected from halogen, alkyl group ($C_1$ to $C_6$), alkoxy group ($C_1$ to $C_6$), nitro group, and hydroxy group, and herbicides containing them as an effective ingredient.

The above terms are illustratively explained as follows: The alkyl group includes methyl, ethyl, propyl, i-propyl, butyl, i-butyl, t-butyl, cyclopropyl, cyclopentyl, and cyclohexyl. The aryl group includes phenyl, tolyl, xylyl, nitrophenyl, halogenophenyl, hydroxyphenyl, and methoxyphenyl. The alkenyl group includes vinyl, allyl, butenyl, butadienyl, cyclohexenyl, and cycloheptenyl. The alkynyl group includes ethynyl, propynyl, and butynyl. The aralkyl group includes benzyl, phenethyl, halogenobenzyl, methoxybenzyl, hydroxybenzyl, nitrobenzyl, α-methylbenzyl, and α,α-dimethylbenzyl. The alkylene group includes tetramethylene, pentamethylene, and hexamethylene. The alkoxy group includes methoxy, ethoxy, propoxy, and butoxy. The alkylthio group includes methylthio, ethylthio, butylthio, cyclopropylthio, and cyclohexylthio. The acyl group includes formyl, acetyl, propionyl, butyryl, isovaleryl, pivaloyl, acryloyl, methacryloyl, benzoyl, toluoyl, cinnamoyl, nicotinoyl, and cyclohexanecarbonyl. The halogen includes chlorine, bromine, and iodine.

As the result of various investigations on the herbicidal activity of various isoxazole derivatives, the present inventors have discovered that the said isoxazole derivatives (I) show an excellent herbicidal activity with a very low toxicity to humans, animals, and fishes. It has also been discovered that the isoxazole derivatives (I) can be smoothly decomposed or degraded in soil to a suitable extent after application. Thus has the present invention been established.

Accordingly, it is a basic object of the present invention to embody the isoxazole derivatives (I). Another object of the invention is to embody the herbicides containing the isoxazole derivatives (I). A further object of the invention is to embody a process for preparing the isoxazole derivatives (I). These and other objects will be apparent to those conversant with the art to which the present invention pertains, from the subsequent description.

The isoxazole derivatives (I) of this invention involve nine types of compounds (Ia, Ib, Ic, Id, Ie, If, Ig, Ih, and Ii), and each compound can be prepared according to the following scheme:

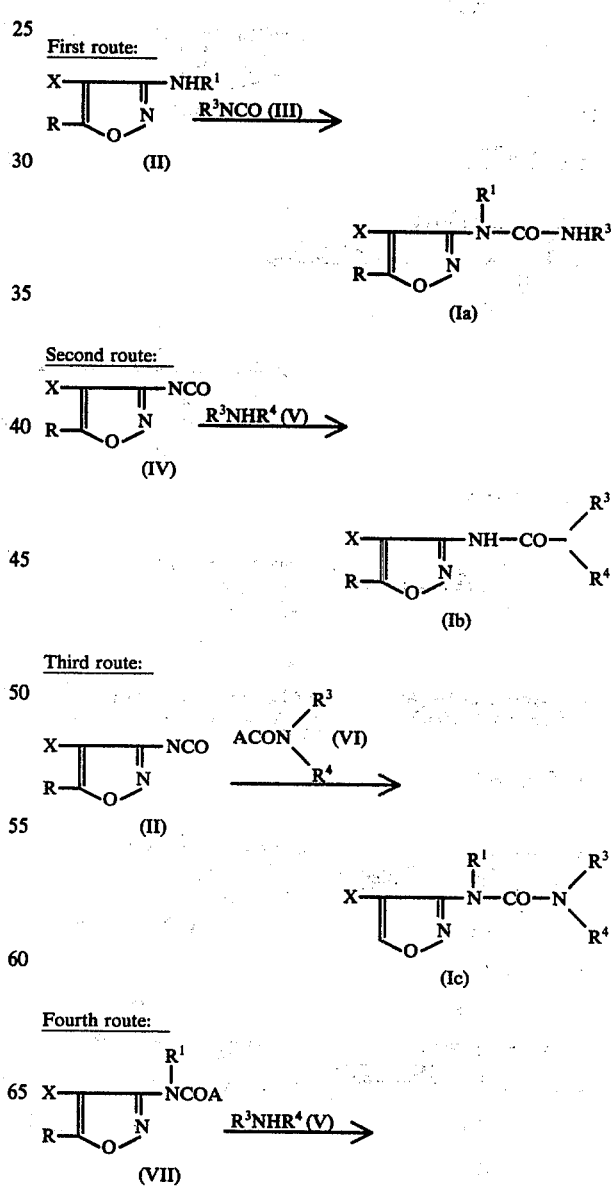

Fifth route:

$$\text{(II)} \xrightarrow{\text{ACOYR}^5 \text{(VIII)}} \text{(Id)}$$

Sixth route:

$$\text{(IV)} \xrightarrow{\text{R}^5\text{YH (IX)}} \text{(Ie)}$$

Seventh route:

$$\text{(VII)} \xrightarrow{\text{R}^5\text{YH (IX)}} \text{(Id)}$$

Eighth route:

Ia, Ib, Ic, Id, Ie, Ig $\xrightarrow{\text{Alkylation}}$ (If)

[At least one hydrogen exists on the N-atom.]   [At least one alkyl group is introduced on the N-atom.]

Ninth route:

$$\text{(II)} \xrightarrow{\text{Acylation}} \text{(Ig: R}^2 = \text{Acyl)}$$

Tenth route:

$$\text{(X)} \xrightarrow{\text{Halogenation}} \text{(Ih: X = Halogen)}$$

Eleventh route:

$$\text{(XI)} \xrightarrow{\text{R}^4 - \text{A}} \text{(Ii: R}^4 = \text{Alkylthio)}$$

wherein A represents a reactive group (e.g., halogen, a residue of ester), and R, $R^1$, $R^2$, $R^3$, $R^4$, $R^5$, X, and Y are each as defined above.

Practical embodiments on the preparation of the isoxazole derivatives (I) in each route are illustrated in the following examples.

EXAMPLE 1

To a solution of 3-amino-5-t-butylisoxazole (16.82 g) in anhydrous benzene (140 ml), methyl isocyanate (8.90 g) and triethylamine (0.5 ml) are added. The resulting mixture is stirred at room temperature for about 8 hours, allowed to stand overnight and refluxed for 1 hour. After ice cooling, the reaction mixture is filtered to give a precipitate, which is recrystallized from ethyl acetate to give 1-methyl-3-(5-t-butyl-3-isoxazolyl)urea (21.61 g) as colorless needles melting at 187.0° to 187.5° C.

EXAMPLES 2 to 65

The reactions are each effected as above, whereby the corresponding products (Ia) are obtained:

Table 1

$$\text{(II)} \xrightarrow{\text{R}^3\text{NCO (III)}} \text{(Ia)}$$

| Syn Ex. | R | X | $R^1$ | $R^3$ | M.P., B.P., or I.R. |
|---|---|---|---|---|---|
| 2 | H | H | H | Me | 165.5–166.0 |
| 3 | Me | H | H | Me | 214.0–215.0 |
| 4 | Et | H | H | Me | 157.5–159.0 |
| 5 | Pr | H | H | Me | 155.0–156.0 |
| 6 | i-Pr | H | H | Me | 112.0–113.0 |
| 7 | C-Pr | H | H | Me | 157.0–158.0 |
| 8 | Ph | H | H | Me | 195.5–196.0 |
| 9 | —(CH$_2$)$_4$— | | H | Me | 193.0–194.0 |
| 10 | Me | H | H | Et | 133.0–134.5 |
| 11 | i-Pr | H | H | Et | 122.5–123.5 |
| 12 | t-Bu | H | H | Et | 179.0–180.5 |
| 13 | Me | H | H | Pr | 95.0–96.7 |
| 14 | i-Pr | H | H | Pr | 88.5–89.5 |
| 15 | t-Bu | H | H | Pr | 134.0–135.0 |
| 16 | Me | H | H | i-Pr | 118.0–119.0 |
| 17 | i-Pr | H | H | i-Pr | 115.0–116.0 |
| 18 | t-Bu | H | H | i-Pr | 134.0–135.0 |
| 19 | Me | H | H | Bu | 89.5–90.5 |
| 20 | i-Pr | H | H | Bu | 71.0–72.0 |
| 21 | t-Bu | H | H | Bu | 69.5–71.5 |
| 22 | Me | H | H | Al | 110.0–111.0 |
| 23 | i-Pr | H | H | Al | 81.82.5 |
| 24 | t-Bu | H | H | Al | 130.0–131.0 |
| 25 | Me | H | H | C—He | 164.0–165.0 |
| 26 | i-Pr | H | H | C—He | 161.5–163.5 |
| 27 | t-Bu | H | H | C—He | 193.5–195.0 |
| 28 | H | H | H | Ph | 187.0–188.0 |
| 29 | Me | H | H | Ph | 188.0–189.0 |
| 30 | Et | H | H | Ph | 157.0–158.5 |
| 31 | Pr | H | H | Ph | 160.0–161.0 |
| 32 | i-Pr | H | H | Ph | 178.0–179.0 |
| 33 | t-Bu | H | H | Ph | 198.5–199.5 |
| 34 | C-Pr | H | H | Ph | 158.5–160.0 |

Table 1-continued $$X\text{-}\underset{O}{\underset{|}{\diagdown}}\overset{NHR^1}{\underset{N}{\diagup}} \quad \xrightarrow{R^3NCO \text{ (III)}}$$

(II)

$$X\text{-}\underset{O}{\underset{|}{\diagdown}}\overset{A^1}{\underset{N}{\diagup}}N\text{-}CO\text{-}NHR^1$$

(Ia)

| Syn Ex. | R | X | R¹ | R³ | M.P., B.P., or I.R. |
|---|---|---|---|---|---|
| 35 | Ph | H | H | Ph | 210.5–211.5 (d) |
| 36 | —(CH₂)₄— | | H | Ph | 187.0–188.0 |
| 37 | Me | H | H | m-Tol | 169.5–170.0 |
| 38 | i-Pr | H | H | m-Tol | 164.5–166.0 |
| 39 | t-Bu | H | H | m-Tol | 188.5–190.0 (d) |
| 40 | Me | H | H | p-Cl—Ph | 205.5–207.0 (d) |
| 41 | i-Pr | H | H | p-Cl—Ph | 174.0–175.0 |
| 42 | t-Bu | H | H | p-Cl—Ph | 188.5–190.5 |
| 43 | Me | H | H | p-Br—Ph | 201.5–203.0 (d) |
| 44 | i-Pr | H | H | p-Br—Ph | 176.0–177.0 (d) |
| 45 | t-Bu | H | H | p-Br—Ph | 192.5 (d) |
| 46 | H | H | Me | Me | 63.0–64.0 |
| 47 | Me | H | Me | Me | 77.0–78.0 |
| 48 | Et | H | Me | Me | 74.0–75.0 |
| 49 | Pr | H | Me | Me | 45.0–46.0 |
| 50 | i-Pr | H | Me | Me | 77.5–78.5 |
| 51 | C-Pr | H | Me | Me | 67.0–68.0 |
| 52 | t-Bu | H | Me | Me | 150.0–151.0 |
| 53 | Ph | H | Me | Me | 132.0–133.0 |
| 54 | —(CH₂)₄— | | Me | Me | 82.5–83.5 |
| 55 | t-Bu | H | Me | 3,4-Cl₂—Ph | 128.5–129.5 |
| 56 | t-Bu | Cl | Me | Me | 155.0–156.0 |
| 57 | Me | H | Et | Me | 37.0–38.0 |
| 58 | t-Bu | H | Me | Bu | 1690, 1607 cm⁻¹ (CCl₄) |
| 59 | i-Bu | H | H | Me | 148.5–149.5 |
| 60 | i-Bu | H | Me | Me | 123–125° C/0.66 mm Hg |
| 61 | i-Bu | H | Me | Al | 139–141° C/0.69 mm Hg |
| 62 | t-Bu | H | Me | Al | 126–128° C/0.45 mm Hg |
| 63 | t-Bu | H | Et | Me | 106.5–107.5 |
| 64 | t-Bu | H | Me | Et | 1683, 1603 cm⁻¹ (CCl₄) |
| 65 | t-Bu | Br | H | Me | 160.5–161.0 |

Note:
The abbreviations used in the above table each have the following significance: H (Hydrogen), Me (methyl group), Et (Ethyl group), Pr (Propyl group), Bu (Butyl group), Ph (Phenyl group), Al (Allyl group), He (Hexyl group), Tol (Tolyl group), C- (Cyclo-), d (Decomposition point), i- (iso-), t- (tertiary), m- (metha-), p- (para-), M.P. (Melting point, ° C), B.P. (Boiling point), I.R. (Infra red adsorption spectre).

EXAMPLE 66

To a suspension of 3-amino-5-cyclopropylisoxazole (1.74 g) in benzene (20 ml), i-propyl chlorocarbonate (2.06 g) is added at room temperature with stirring in 5 to 10 minutes. The resultant mixture is mixed with pyridine (1.22 g) under ice cooling for 30 minutes and allowed to stand at room temperature overnight. After cooling, the reaction mixture is mixed with water (20 ml) and shaken with benzene. The benzene layer is washed with water thrice, dried over anhydrous sodium sulfate and evaporated to remove the benzene. Thus-obtained crystals (2.97 g) are recrystallized from hexane to give i-propyl N-(5-cyclopropyl-3-isoxazolyl)carbamate as light yellow prisms melting at 64.5° to 65.5° C. The yield is 92.9%.

EXAMPLES 67 to 83

The reactions are effected as in Example 66, whereby the corresponding products (Id) are obtained:

Table 2

$$X\text{-}\underset{O}{\underset{|}{\diagdown}}\overset{R^1}{\underset{N}{\diagup}}N\text{-}COOR^5$$

(Id)

| Syn. Ex. | R | X | R¹ | R⁵ | M.P., B.P., or I.R. |
|---|---|---|---|---|---|
| 67 | Me | H | H | Me | 136.0–137.0 |
| 68 | Et | H | H | Me | 83.0–84.0 |
| 69 | Pr | H | H | Me | 66.0–67.0 |
| 70 | i-Pr | H | H | Me | 74.0–75.0 |
| 71 | t-Bu | H | H | Me | 57.5–58.5 |
| 72 | H | H | H | i-Pr | 87.5–89.0 |
| 73 | Me | H | H | i-Pr | 82.0–82.5 |
| 74 | i-Pr | H | H | i-Pr | 56.0–58.0 |
| 75 | t-Bu | H | H | i-Pr | 83.0–83.5 |
| 76 | Ph | H | H | i-Pr | 103.5–104.5 |
| 77 | —(CH₂)₄— | | H | i-Pr | 129.0–130.0 |
| 78 | C—Pr | H | H | Me | 101.5–102.5 |
| 79 | Me | H | Me | Me | 85–95° C (bath temp.)/0.80 mm Hg |
| 80 | i-Bu | H | H | Me | 76.0–77.0 |
| 81 | t-Bu | H | H | Et | 51.0–52.0 |
| 82 | H | H | H | Me | 124–125 |
| 83 | t-Bu | H | Me | Me | 84.0–87.0° C/0.55 mm Hg |

Note:
The abbreviations in the table are each as described above.

EXAMPLE 84

Dimethyl pyrocarbonate (28.16 g) is added to 3-amino-5-methylisoxazole (19.62 g) at room temperature with stirring to give a solution with vesication. The solution is slightly warmed to initiate the reaction exothermically. The reaction mixture is allowed to stand for 2 hours, and the precipitated crystals are filtered and washed with methanol (15 ml) to give crude crystals (17.31 g). The filtrate is combined with the washings and evaporated under reduced pressure to give second crystals (1.56 g). Both crude crystals are combined and recrystallized from methanol to give methyl N-(5-methyl-3-isoxazolyl)carbamate (14.70 g) as crystals melting at 136.0° to 137.0° C.

EXAMPLE 85

Dimethyl pyrocarbonate (4.02 g) is added to 3-amino-5-t-butylisoxazole (2.80 g), and the resulting mixture is stirred at room temperature for 40 minutes and 1 hour, then stirred at 65° C. for 3 hours. Dimethyl pyrocarbonate (1.34 g) is still added, and the resulting mixture is stirred at 65° C. for 1 hour. The reaction mixture is cooled to room temperature, allowed to stand overnight and evaporated under reduced pressure. The residue (4.02 g) is recrystallized from hexane to give methyl N-(5-t-butyl-3-isoxazolyl)carbamate as crystals melting at 55.5° to 58.5° C.

EXAMPLE 86

Dimethyl carbonate (2.38 g) and sodium methoxide (0.30 g) are added to 3-amino-5-methylisoxazole (0.49 g), and the resultant mixture is stirred at 100° C. for 3 hours. After cooling, the reaction mixture is combined with water (15 ml), adjusted to pH 1 with a small amount of c. hydrochloric acid and shaken twice with ethyl acetate. The organic layer is washed with water, dried over anhydrous sodium sulfate and evaporated to remove the solvent. The resulting light yellow crystals (0.52 g) are chromatographed on a column of silica gel, whereby methyl N-(5-methyl-3-isoxazolyl)carbamate is obtained as crystals melting at 136.0° to 137.0° C.

EXAMPLE 87

To a suspension of 5-t-butyl-3-isoxazolyl isocyanate (1.99 g) in benzene (120 ml), N-methylbutylamine (1.15 g) is added, and the resultant mixture is refluxed for 3 hours. After cooling, the reaction mixture is evaporated to remove the solvent, and the residue is chromatographed on a plate of silica gel to give 1-butyl-1-methyl-3-(5-t-butyl-3-isoxazolyl)urea (2.73 g). This substance is recrystallized from hexane to give crystals melting at 65.5° to 66.5° C. The yield is 89.8%.

EXAMPLES 88 to 155

The reactions are each effected as in Example 87 to give the corresponding product (Ib):

Table 3.

$$\underset{R}{\overset{X}{\diagdown}}\underset{O}{\overbrace{\phantom{xxx}}}\overset{N}{\diagup}\text{NH}-\text{CO}-\text{N}\overset{R^3}{\underset{R^4}{\diagdown}}\qquad(Ib)$$

| Syn. Ex. | R | X | R³ | R⁴ | M.P., B.P., or I.R., |
|---|---|---|---|---|---|
| 88 | t-Bu | H | Me | Me | 119.5–120.5 |
| 89 | Me | H | H | H | 201–203 (d) |
| 90 | t-Bu | H | H | H | 179.5–180.5 |
| 91 | Me | H | Me | Me | 150.5–151.5 |
| 92 | t-Bu | H | Me | Al | 90.0–91.0 |
| 93 | t-Bu | H | Me | Met | 106.0–107.0 |
| 94 | Me | H | —CH₂CH₂\O/—CH₂CH₂ | | 170.0–171.0 |
| 95 | i-Pr | H | Me | Me | 69.0–70.0 |
| 96 | i-Bu | H | Me | Me | 90.5–91.0 |
| 97 | i-Pr | H | Me | Bu | 1680, 1616 cm⁻¹ (CCl₄) |
| 98 | i-Bu | H | Me | Bu | 1678, 1620 cm⁻¹ (CCl₄) |
| 99 | t-Bu | H | Me | Et | 88.5–89.5 |
| 100 | t-Bu | H | Et | Et | 122.0–123.5 |
| 101 | t-Bu | H | Pr | Pr | 75.0–80.5 |
| 102 | t-Bu | H | i-Pr | i-Pr | 200–205 (d) |
| 103 | t-Bu | H | Et | Bu | 1677, 1612 cm⁻¹ (CCl₄) |
| 104 | t-Bu | H | Me | C—He | 149.5–150.5 |
| 105 | t-Bu | H | Me | Ph | 122.5–123.0 |
| 106 | t-Bu | H | Me | Bz | 107.0–108.0 |
| 107 | t-Bu | H | Al | Al | 1676, 1610 cm⁻¹ (CCl₄) |
| 108 | t-Bu | H | Bu | Bu | 1676, 1611 cm⁻¹ (CCl₄) |
| 109 | t-Bu | H | i-Bu | i-Bu | 112.0–113.0 |
| 110 | Me | H | Me | Bu | 79.0–80.0 |
| 111 | Me | H | Me | Al | 89.0–90.0 |
| 112 | Me | H | Me | Met | 91.0–92.0 |
| 113 | Me | H | H | o-F-Pn | 170.0–171.0 |
| 114 | Me | H | H | 3,4-Cl₂—Ph | 208.0–209.0 |
| 115 | Me | H | H | p-NO₂-Ph | 253–254 (d) |
| 116 | Me | H | —(CH₂)₄— | | 193.0–194.0 |
| 117 | Me | H | —(CH₂)₅— | | 159.0–160.0 |
| 118 | WEt | H | Me | Me | 86.5–87.5 |
| 119 | Et | H | Me | Bu | 1682, 1624 cm⁻¹ (CCl₄) |
| 120 | Et | H | Me | Al | 46.5–47.5 |
| 121 | Et | H | Me | Met | 67.0–68.0 |
| 133 | Et | H | —(CH₂)₂O(CH₂)₂— | | 121.5–122.0 |
| 123 | Pr | H | Me | Me | 88.0–89.0 |
| 124 | Pr | H | Me | Bu | 1680, 1622 cm⁻¹ (CCl₄) |
| 125 | Pr | H | Me | Al | 55.0–57.0 |
| 126 | Pr | H | Me | Met | 64.0–65.0 |
| 127 | Pr | H | —(CH₂)₂O(CH₂)₂— | | 108.5–109.0 |
| 128 | i-Pr | H | Me | Al | 55.5–56.5 |
| 129 | i-Pr | H | Me | Met | 54.4–55.0 |
| 130 | i-Pr | H | —(CH₂)₂O(CH₂)₂— | | 130.5–131.5 |
| 131 | i-Bu | H | Me | Al | 25.5–27.0 |
| 132 | i-Bu | H | Me | Met | 92.0–83.0 |
| 133 | i-Bu | H | —(CH₂)₂O(CH₂)₂— | | 109.5–110.5 |
| 134 | t-Bu | H | H | s-Bu | 132.5–134.0 |
| 135 | t-Bu | H | H | i-Bu | 121.5–122.0 |
| 136 | t-Bu | H | H | t-Bu | 180.5–183.5 |
| 137 | t-Bu | H | H | 3,4-Cl₂—Ph | 226.5–227.0 |
| 138 | t-Bu | H | H | Bz | 136.5–137.5 |
| 139 | t-Bu | H | H | α-Me—Bz | 118.0–119.0 |

Table 3.-continued $$\underset{R}{\overset{X}{\diagdown}}\underset{O}{\overbrace{\phantom{xxx}}}\overset{N}{\diagup}\text{NH}-\text{CO}-\text{N}\overset{R^3}{\underset{R^4}{\diagdown}}\qquad(Ib)$$

| Syn. Ex. | R | X | R³ | R⁴ | M.P., B.P., or I.R., |
|---|---|---|---|---|---|
| 140 | t-Bu | H | Me | Pr | 76.0–77.0 |
| 141 | t-Bu | H | Me | i-Pr | 90.5–91.5 |
| 142 | t-Bu | H | Me | s-Bu | 113.5–114.5 |
| 143 | t-Bu | H | Me | i-Bu | 113.5–114.5 |
| 144 | t-Bu | H | Me | t-Bu | 149.0–151.0 |
| 145 | t-Bu | H | Me | He | 1679, 1615 cm⁻¹ (CCl₄) |
| 146 | t-Bu | H | Me | α-Me—Bz | 121.0–122.0 |
| 147 | C—Pr | H | Me | Me | 145.0–146.0 |
| 148 | C—Pr | H | Me | Met | 77.5–78.5 |
| 149 | Ph | H | Me | Me | 183.0–185.0 |
| 150 | Ph | H | Me | Met | 128.0–129.0 |
| 151 | —(CH₂)₄— | | Me | Me | 164.5–165.5 |
| 152 | —(CH₂)₄— | | Me | Met | 111.5–112.0 |
| 153 | t-Bu | H | —(CH₂)₄— | | 132.0–137.5 |
| 154 | t-Bu | H | —(CH₂)₅— | | 114.0–115.0 |
| 155 | t-Bu | H | —(CH₂)₂O(CH₂)₂— | | 179.0–180.0 |

Note:
The abbreviations each are the following significance: Met (Methoxy group), Bz (Benzyl group). The others are as defined above.

EXAMPLES 156 to 166

To a suspension of 5-methyl-3-isoxazolyl isocyanate (1.71 g) in benzene (46 ml), allyl alcohol (0.88 g) is added, and the resultant mixture is refluxed for 3 hours. After cooling, the reaction mixture is evaporated to remove the solvent, whereby allyl N-(5-methyl-3-isoxazolyl)carbamate (2.38 g) is obtained. This substance is recrystallized from cyclohexane to give crystals melting at 76.5° to 77.5° C.

The reactions are each effected as above to give the corresponding products (Ie):

Table 4.

$$\underset{t\text{-Bu}}{\overset{X}{\diagdown}}\underset{O}{\overbrace{\phantom{xxx}}}\overset{N}{\diagup}\text{NH}-\text{CO}-\text{Y}-\text{R}^5\qquad(Ie)$$

| Sy. Ex. | X | Y | R⁵ | M.P., B.P., or I.R. |
|---|---|---|---|---|
| 157 | H | O | —CH₂C≡CH | 126.5–127.5 |
| 158 | H | S | Me | 115.5–116.5 |
| 159 | H | S | Ph | 154.0–155.0 |
| 160 | H | O | —CH₂CCl₃ | 151.5–152.5 |
| 161 | H | O | —CH₂CH=CH₂ | 64.0–65.0 |
| 162 | H | O | Pr | 87.5–88.5 |
| 163 | H | O | —CH₂CH₂OH | 1740, 1611 cm⁻¹ (CCl₄) |
| 164 | H | O | —CH₂CH₂OCH₃ | 49–51 |
| 165 | H | O | α,α-Me₂—Bₓ | 126.0–128.0 |
| 166 | H | O | —CH₂CF₃ | 125.0–126.0 |

Note:
The abbreviations are each as defined above.

EXAMPLE 167

To the sodium methoxide obtained by mixing sodium (1.57 g) with anhydrous methanol (45 ml), methyl N-(5-t-butyl-3-isoxazolyl)carbamate (12.88 g) is added. The resultant mixture is stirred at room temperature for 10 minutes, and the methanol is evaporated under reduced pressure. The residue is mixed with anhydrous benzene (100 ml) and dimethyl sulfate (8.61 g). The resultant mixture is stirred for 1 hour and refluxed for 1 hour. After cooling, the precipitate is filtered off. The organic layer is washed with an aqueous saturated solution of sodium bicarbonate and water in order, dried over anhydrous sodium sulfate, and the solvent is evaporated. The residue is distilled to give methyl N-methyl-N-(5-t- butyl-3-isoxazolyl)carbamate (11.45 g) as a distillate boiling at 84.0° to 87.0° C./0.55 mm Hg.

EXAMPLES 168 to 170

The reactions are each effected as in Example 167 to give the corresponding products (If):

Table 5

$$\underset{R}{\overset{X}{\rule{0pt}{0pt}}}\!\!\!\diagdown\!\!\!\overset{R^1}{\underset{O}{\rule{0pt}{0pt}}}\!\!\!\!\diagup\!\!\!N\!\!-\!\!R^2 \qquad (If)$$

| Syn. Ex. | R | X | R¹ | R² | Product (If) M.P., B.P., or I.R. |
|---|---|---|---|---|---|
| 168 | C—Pr | H | Me | —COOCH₃ | 96–97.5° C/0.5 mmHg |
| 169 | i-Bu | H | Me | —COCH₃ | 98–100° C/0.42 mm Hg |
| 170 | Me | Cl | Me | —COCH₃ | 92–83° C (bath temp.)/0.36 mm Hg |

Note:
The abbreviations are each as defined above.

EXAMPLE 171

To a solution of 1,1-dimethyl-3-(5-t-butyl-3-isoxazolyl)urea (10.99 g) in dry dimethylformamide (10 ml), 50% sodium hydride (2.75 g) is added at room temperature with stirring, and the resultant mixture is heated at 60° C. for 15 minutes. A solution of methyl iodide (8.86 g) in dry dimethylformamide (30 ml) is added at 10° C. in 1 hour thereto, and the mixture is heated at 80° C. for 5 minutes and evaporated to remove the solvent. The residue is combined with water and shaken with chloroform. The chloroform layer is dried over anhydrous sodium sulfate and the solvent is evaporated. The residue is chromatographed on a column of silica gel to give 1,1,3-trimethyl-3-(5-t-butyl-3-isoxazolyl)urea (10.94 g) as crystals melting at 90° to 91.0° C. The yield is 93.38%.

EXAMPLES 172 to 178

The reactions are each effected as in Example 171 to give the corresponding products (If):

Table 6

$$\underset{R}{\overset{X}{\rule{0pt}{0pt}}}\!\!\!\diagdown\!\!\!\overset{R^1}{\underset{O}{\rule{0pt}{0pt}}}\!\!\!\!\diagup\!\!\!N\!\!-\!\!R^2 \qquad (If)$$

| Syn. Ex. | R | X | R¹ | R² | Product (If) M.P., B.P., or I.R. |
|---|---|---|---|---|---|
| 172 | Me | H | Me | —CON(CH₃)₂ | 105–108° C (bath temp.)/10.48 mm Hg |
| 173 | Et | H | Me | —CON(CH₃)₂ | 113.0–114.0° C/0.85 mm Hg |
| 174 | Pr | H | Me | —CON(CH₃)₂ | 115.0–116.0° C/0.60 mm Hg |
| 175 | i-Pr | H | Me | —CON(CH₃)₃ | 106.0–107.0° C/0.30 mm Hg |
| 176 | i-Bu | H | Me | —CON(CH₃)₂ | 123.0–124.0° C/0.54 mm Hg |
| 177 | C—Pr | H | Me | —CON(CH₃)₂ | 130.0–131.0° C/0.58 mm Hg |
| 178 | Ph | H | Me | —CON(CH₃)₂ | 1681, 1623 cm⁻¹ (CCl₄) |

Note:
The abbreviations are each as defined above.

EXAMPLE 179

The reaction is effected as in Example 171 by using 1-(5-methyl-3-isoxazolyl)urea to give 1,3-dimethyl-3-(5-methyl-3-isoxazolyl)urea as crystals melting at 77.0° to 78.0° C. in a yield of 2.1% and 1-methyl-1-(5-methyl-3-isoxazolyl)urea as crystals melting at 146.0° to 147.0° C. in a yield of 48.5%. Still, 3-methylamino-5-methylisoxazole is prepared in a form of side product as crystals melting at 55.0° to 56.0° C. in a yield of 17.7%.

EXAMPLE 180

The reaction is effected as in Example 171 by using 1-(5-t-butyl-3-isoxazolyl)urea to give 1,1,3-trimethyl-3-(5-t-butyl-3-isoxazolyl)urea as crystals melting at 90.0° to 91.0° C. in a yield of 5.61%, 1,3-dimethyl-3-(5-t-butyl-3-isoxazolyl)urea as crystals melting at 150.0° to 151.0° C. in a yield of 7.24% and 1-methyl-1-(5-t-butyl-3-isoxazolyl)urea as crystals melting at 134.0° to 135.0° C. in a yield of 46.97%. Still, 3-methylamino-5-t-butylisoxazole is obtained as a distillate boiling at 83° C./0.71 mm Hg as a side product in a yield of 14.30%.

EXAMPLE 181

The reaction is effected as in Example 171 by using 1-methyl-3-(5-t-butyl-3-isoxazolyl)urea to give 1,3-dimethyl-3-(5-t-butyl-3-isoxazolyl)urea as crystals melting at 150° to 151.0° C. in a yield of 16.3% and 1,1,3-trimethyl-3-(5-t-butyl-3-isoxazolyl)urea as crystals melting at 90.0° to 91.0° C. in a yield of 33.9%.

EXAMPLE 182

The reaction is effected as in Example 167 by using 1-methyl-3-(5-methyl-3-isoxazolyl)urea to give 1,3-dimethyl-3-(5-methyl-3-isoxazolyl)urea as crystals melting at 77.0° to 78.0° C. in a yield of 58.3%.

EXAMPLE 183

The reaction is effected as in Example 171 by using 1-methyl-1-butyl-3-(5-t-butyl-3-isoxazolyl)urea and methyl iodide to give 1,3-dimethyl-1-butyl-3-(5-t-butyl-3-isoxazolyl)urea as an oil boiling at 130° to 135° C. (bath temperature)/0.25 mm Hg.

EXAMPLE 184

The reaction is effected as in Example 171 by using 1-methyl-1-butyl-3-(5-t-butyl-3-isoxazolyl)urea and ethyl iodide to give 1-methyl-1-butyl-3-ethyl-3-(5-t-butyl-3-isoxazolyl)urea as an oil boiling at 130° to 135° C. (bath temperature)/0.25 mm Hg.

EXAMPLE 185

The reaction is effected as in Example 171 by using 1-ethyl-1-butyl-3-(5-t-butyl-3-isoxazolyl)urea and methyl iodide to give 1-ethyl-1-butyl-3-methyl-3-(5-t-butyl-3-isoxazolyl)urea as an oil boiling at 140° to 145° C. (bath temperature)/0.67 mm Hg.

EXAMPLE 186

To 3-amino-5-methylisoxazole (490.6 mg), pyridine (3 g) and dimethylcarbamoyl chloride (1.18 g) are added, and the resultant mixture is stirred at 60° C. for 5.5 hours. The pyridine is evaporated under reduced pressure. The residue is mixed with water (15 ml), adjusted to pH 1 with 5% hydrochloric acid and shaken with chloroform. The chloroform layer is evaporated to remove the chloroform. The residue is mixed with 1.5% methanolic sodium hydroxide solution (25 ml) and evaporated. The residue is extracted with chloroform again. The organic layer is washed with water, dried over anhydrous sodium sulfate and evaporated to remove the chloroform. The residue is chromatographed on a thin layer of silica gel to give 1,1-dimethyl-3-(5-methyl-3-isoxazolyl)urea (0.4735 g) as crystals melting at 150.5° to 151.5° C. The yield is 56%.

EXAMPLE 187

The reaction is effected as in Example 186 by using 3-methylamino-5-t-butylisoxazole to give 1,1,3-trimethyl-3-(5-t-butyl-3-isoxazolyl)urea as crystals melting at 90.0° to 91.0° C.

EXAMPLE 188

To 3-amino-5-methylisoxazole (10.0 g), 99% formic acid (47.0 g) is added, and the resultant mixture is refluxed for 1 hour with stirring. The reaction mixture is evaporated under reduced pressure to remove the formic acid. The residue is mixed with icy water (50 ml), and the precipitated crystals are filtered. The crystals are washed with water and dried under reduced pressure to give 3-formylamino-5-methylisoxazole (12.06 g). This substance is recrystallized from methanol to give crystals melting at 130.5° to 131° C.

EXAMPLES 189 to 197

The reactions are each effected as in Example 188, whereby the corresponding products (Ig) are obtained:

Table 6.

$$X-\underset{R-O-N}{\overset{}{\underset{}{\bigsqcup}}}-NH-CHO \quad (Ig)$$

| Syn Exc. | R | X | M.P., B.P., or I.R. |
|---|---|---|---|
| 189 | H | H | 104–105 |
| 190 | Me | H | 130.5–131.9 |
| 191 | Et | H | 67–69 |
| 192 | Pr | H | 84.5–85.5 |
| 193 | i-Pr | H | 125–134° C (bath temp.)/0.4–0.42 |
| 194 | t-Bu | H | 130–140° C (bath temp.)/0.73–0.74 mm Hg |
| 195 | C-Pr | H | 92.3–93.3 |
| 196 | Ph | H | 132–133 |
| 197 | —(CH$_2$)$_4$— | | 152–166° C (bath temp.)/0.69–0.65 mm Hg |

Note: the abbreviations are each as defined above.

EXAMPLE 198

To 3-amino-5-t-butylisoxazole (2.80 g), acetic anhydride (6 ml) is added, and the resultant mixture is allowed to stand at room temperature for 4 hours. The reaction mixture is mixed with chilled water (50 ml), and the precipitated crystals are filtered. The crystals are washed with water and dried to give 3-acetylamino-5-t-butylisoxazole (3.39 g). This substance is recrystallized from hexane to give crystals melting at 120.5° to 121.0° C.

EXAMPLES 199 to 203

The reactions are each effected as in Example 198, whereby the corresponding products (Ig) are obtained:

Table 7

$$X-\underset{R-O-N}{\overset{R^1}{\underset{}{\bigsqcup}}}-N-R^2 \quad (Ig)$$

| Syn. Ex. | R | X | R$^1$ | R$^2$ | M.P., B.P., or I.R. |
|---|---|---|---|---|---|
| 199 | Me | H | Me | —COCH$_3$ | 88–92° C/0.95 mm Hg |
| 200 | 5-Bu | H | H | —COCF$_3$ | 145.0–145.5 |
| 201 | t-Bu | H | H | —COCF$_2$CF$_3$ | 103.0–104.0 |
| 202 | t-Bu | H | Me | —COC$_2$H$_5$ | 111–116° C (bath temp.)/0.45 mm Hg |
| 203 | Me | Cl | H | —COCH$_3$ | 122.0–122.5 |

Note: The abbreviations are each as defined above.

EXAMPLE 204

To a solution of 3-amino-5-t-butylisoxazole in benzene, benzoyl chloride and pyridine are added, whereby the reaction is carried out. Thus 3-benzoylamino-5-t-butylisoxazole is obtained as crystals melting at 192° to 193° C.

EXAMPLES 205 to 208

The reactions are each effected as in Example 204, whereby the corresponding products (Ig) are obtained:

Table 8.

$$X-\underset{R-O-N}{\overset{R^1}{\underset{}{\bigsqcup}}}-N-R^2 \quad (Ig)$$

| Syn Ex. | R | X | R$^1$ | R$^2$ | M.P., B.P., or I.R. |
|---|---|---|---|---|---|
| 205 | t-Bu | H | H | —COCH$_2$Cl | 105.5–106.5 |
| 206 | t-Bu | H | H | —COCHCl$_2$ | 124.0–125.0 |
| 207 | t-Bu | H | H | —CO-t-Bu | 174.5–175.5 |
| 208 | t-Bu | H | i-Pr | —COCH$_2$Cl | 1686, 1585 cm$^{-1}$ (CCl$_4$) |

Note: The abbreviations are each as defined above.

EXAMPLE 209

To a solution of 1-methyl-3-(5-t-butyl-3-isoxazolyl)urea (1.97 g) in pyridine (30 ml), butylsulfenyl chloride (1.08 mol equivalent) is added at −30° to −40° C. The resultant mixture is allowed to stand at −30° to −40° C. for 6 hours and at room temperature overnight. The reaction mixture is chromatographed on a column of silica gel, whereby 1-methyl-1-butylthio-3-(5-t-butyl-3-isoxazolyl)urea (0.31 g) is obtained as an oil. I.R.: 1698, 1606 cm$^{-1}$ (CCl$_4$).

EXAMPLE 210

The reaction is effected as in Example 209 by using 1-methyl-3-(5-methyl-3-isoxazolyl)urea, whereby 1-methyl-1-butylthio-3-(5-methyl-3-isoxazolyl)urea is obtained as an oil. I.R.: 1693, 1618 cm$^{-1}$ (CCl$_4$).

EXAMPLE 211

To a solution of methyl 5-t-butyl-3-isoxazolyl-carbamate (2.00 g) and anhydrous sodium acetate (1.1 mol equivalent) in glacial acetic acid (5 ml), bromine (1.0 mol equivalent) is added. The resultant mixture is heated at 50° C. for 53 hours and mixed with glacial acetic acid (5 ml), anhydrous sodium acetate (0.91 g) and bromine (0.81 g). The mixture is heated at 70° C. for 31 hours, mixed with several drops of formic acid, poured onto icy water (50 ml) and shaken with methylene chloride. The organic layer is washed with a saturated aqueous solution of sodium bicarbonate and water in order and evaporated under reduced pressure to remove the solvent, whereby methyl 4-bromo-5-t-butyl-3-isoxazolyl-carbamate (2.77 g) is obtained as an oil. I.R.: 1774, 1203 cm$^{-1}$ (CCl$_4$).

EXAMPLE 212

The reaction is effected as in Example 211 by using 1,1-dimethyl-3-(5-t-butyl-3-isoxazolyl)urea, whereby 1,1-dimethyl-3-(4-bromo-5-t-butyl-3-isoxazolyl)urea is obtained as crystals melting at 164.5° to 165.5° C.

The isoxazole derivatives (I) show an excellent herbicidal activity against various grasses at a small application rate, and they can also be used as a non-selective or selective herbicide by changing the application rate of the effective compound. The herbicides of this invention are generally applicable over various crops including wheat, barley, corn, carrot, peanut, peas or rice plant for protecting them from unfavorable weeds and grasses. Still, they can be applicable over sugar cane, potato, sweet potato, mentha, egg-plant, or Spanish paprika after their planting. There is essentially no harm caused by the present herbicides on these crops, and if any, only very slight harm is observed, to an extent which permits easy recovery by the crops. Further the present herbicides are harmless and safe to humans and domestic animals, and they show a very low toxicity to fishes and shells. Accordingly, the herbicides of this invention are of very high safety and show a suitable residual degree in soil.

The isoxazole derivatives (I) of this invention may be converted into a suitable alkali metal or alkali earth metal salt before use for requirement in preparation or for improving their stability when they have an active hydrogen on the nitrogen atom.

The herbicidal compositions may be prepared by mixing the effective isoxazole derivative (I) with an inert solid or liquid carrier, optionally in combination with a further adjuvant (e.g., emulsifiers, stabilizers, dispersants, suspending agents, spreaders, penetrants, wetting agents) and converting the resultant mixture into a desired form of preparation (e.g., emulsions, wettable powders, granules, dusts, pills). Examples of the carrier are a solid carrier (e.g., clay, talc, diatomaceous earth, bentonite) and a liquid carrier (e.g., water, alcohols, acetone, benzene, toluene, xylene, solvent naphtha, cyclohexane).

The herbicides of this invention may be used in combination with agricultural chemicals (e.g., insecticides, fungicides, other herbicides), manuring ingredients (e.g., ammonium sulfate, urea), or soil treating agents.

Herbicidal activities of the present herbicides are illustrated by the following experimental examples.

EXPERIMENT 1

Experiment 1.

a) compounds tested:

| Compound No. | Compound Name |
|---|---|
| 1 | 1-Methyl-3-(5-i-propyl-3-isoxazolyl)urea |
| 2 | 1-Methyl-3-(5-t-butyl-3-isoxazolyl)urea |
| 3 | Methyl N-(5-t-butyl-3-isoxazolyl)carbamate |
| 4 | 1,1-Dimethyl-3-(5-t-butyl-3-isoxazolyl)urea |
| 5 | 1,3-Dimethyl-3-(5-t-butyl-3-isoxazolyl)urea |
| 6 | 1,1,3-Trimethyl-3-(5-t-butyl-3-isoxazolyl)urea |
| 7 | 1-Methyl-1-butyl-3-(5-t-butyl-3-isoxazolyl)urea |
| 8 | 1-Allyl-1-methyl-3-(5-t-butyl-3-isoxazolyl)urea |

Experiment 1.-continued a) compounds tested:

| Compound No. | Compound Name |
|---|---|
| 9 | Methyl N-5-t-butyl-3-isoxaxolyl thiolcarbamate |
| 10 | 1-Methoxy-1-methyl-3-(5-t-butyl-3-isoxazolyl)urea |
| 11 | 1,1-Dimethyl-3-(5-i-propyl-3-isoxazolyl)urea |
| 12 | 1-Butyl-1-methyl-3-(5-i-propyl-3-isoxazolyl)urea |
| 13 | 1,1-Diallyl-3-(5-t-butyl-3-isoxazolyl)urea |
| 14 | N-(5-t-Butyl-3-isoxazolyl)morpholinocarbonamide |
| 15 | 1-Butylthio-1-methyl-3-(t-butyl-3-isoxazolyl)urea |
| 16 | 1-Methoxy-1-methyl-3-(5-i-propyl-3-isoxazolyl)urea |
| 17 | PCP-Na (Sodium pentachlorophenoxide) |

(b) Test method (1) Pre-emergence test

In a polyethylene cup (diameter: 9 cm) in which sandy soil was charged, 25 granules of the seed of the test plant were sown. After sowing, the seed was covered with sandy soil in about 5 mm of thickness, and soon an aqueous suspension of the test compound made by using as a spreader Tween 20 (Trademark of Atlas Powder Co.) at a concentration of 100 ppm was applied over the surface of the sandy soil. Application rate of the test compound was 10 g/are and 30 g/are, and the aqueous suspension (water dilution: 10 L/are) was applied by a sprayer. Administration was effected at 25° C. in a greenhouse in the natural sunlight. Degree of the germination was measured 3 weeks after the application.

(2) Post-emergence test

As in the pre-emergence test, the test compound was applied to young plants 10 days after seeding. Administration and measurement were effected as described above.

(c) Method of the evaluation

The result was obtained by observing the plant with the naked eye after the application and calculating the survival ratio of the number of living plants three weeks later. The evaluation was marked in 6° on a survival ratio, as follows:

| Survival ratio of the plant tested | Mark(s) |
|---|---|
| Not more than 10 % | 5 |
| 11–25 % | 4 |
| 26–50 % | 3 |
| 51–75 % | 2 |
| 76–90 % | 1 |
| Not less than 91 % | 0 |

(d) Result

Table 6

| Compond No. | Application rate (g/are) | Herbicidal Activity | | | | | | | | | | | |
|---|---|---|---|---|---|---|---|---|---|---|---|---|---|
| | | Pre-emergence test | | | | | | Post-emergence test | | | | | |
| | | A | B | C | D | E | F | A | B | C | D | E | F |
| 1 | 10 | 0 | 1 | 3 | 5 | 3 | 5 | 0 | 1 | 1 | 5 | 4 | 5 |
| | 30 | 0 | 3 | 4 | 5 | 3 | 5 | 0 | 4 | 5 | 5 | 5 | |
| 2 | 10 | 0 | 2 | 5 | 4 | 5 | 5 | 0 | 5 | 5 | 5 | 5 | 5 |
| | 30 | 0 | 3 | 5 | 5 | 5 | 5 | 0 | 5 | 5 | 5 | 5 | 5 |
| 3 | 10 | 0 | 0 | 2 | 4 | 3 | 2 | 0 | 0 | 3 | 5 | 5 | 3 |
| | 30 | 0 | 2 | 3 | 5 | 5 | 5 | 0 | 0 | 4 | 5 | 5 | 5 |
| 4 | 10 | 1 | 5 | 4 | 5 | 5 | 5 | 0 | 5 | 5 | 5 | 5 | 5 |
| | 30 | 1 | 5 | 5 | 5 | 5 | 5 | 1 | 5 | 5 | 5 | 5 | 5 |
| 5 | 1 | 5 | 5 | 5 | 5 | 5 | 1 | 5 | 5 | 5 | 5 | 5 | |
| | 30 | 1 | 5 | 5 | 5 | 5 | 5 | 1 | 5 | 5 | 5 | 5 | 5 |
| 6 | 10 | 0 | 2 | 4 | 5 | 5 | 3 | 0 | 4 | 5 | 5 | 5 | 5 |
| | 30 | 0 | 3 | 5 | 5 | 5 | 5 | 0 | 5 | 5 | 5 | 5 | 5 |
| | 10 | 0 | 3 | 4 | 5 | 5 | 5 | 0 | 5 | 5 | 5 | 5 | 5 |

Table 6-continued

| Compound No. | Application rate (g/are) | Herbicidal Activity Pre-emergence test | | | | | | Post-emergence test | | | | | |
|---|---|---|---|---|---|---|---|---|---|---|---|---|---|
| | | A | B | C | D | E | F | A | B | C | D | E | F |
| 7 | 30 | 1 | 5 | 5 | 5 | 5 | 5 | 0 | 5 | 5 | 5 | 5 | 5 |
|   | 10 | 0 | 4 | 4 | 5 | 5 | 5 | 0 | 2 | 3 | 5 | 5 | 5 |
| 8 | 30 | 1 | 5 | 5 | 5 | 5 | 5 | 2 | 5 | 5 | 5 | 5 | 5 |
|   | 10 | 0 | 1 | 5 | 5 | 5 | 3 | 0 | 3 | 4 | 5 | 5 | 5 |
| 9 | 30 | 0 | 2 | 5 | 5 | 5 | 3 | 0 | 2 | 5 | 5 | 5 | 5 |
|   | 10 | 0 | 4 | 5 | 5 | 5 | 0 | 2 | 3 | 5 | 5 | 5 |   |
| 10 | 30 | 2 | 5 | 5 | 5 | 5 | 5 | 4 | 5 | 5 | 5 | 5 | 5 |
| 11 | 10 | 0 | 2 | 3 | 5 | 4 | 5 | 0 | 1 | 3 | 5 | 5 | 5 |
| 11 | 30 | 0 | 5 | 5 | 5 | 5 | 5 | 0 | 5 | 5 | 5 | 5 | 5 |
|   | 10 | 0 | 3 | 3 | 5 | 4 | 5 | 0 | 1 | 3 | 5 | 5 | 5 |
| 12 | 30 | 0 | 5 | 5 | 5 | 5 | 5 | 0 | 2 | 5 | 5 | 5 | 5 |
|   | 10 | 0 | 0 | 0 | 5 | 2 | 5 | 0 | 1 | 3 | 5 | 5 | 5 |
| 13 | 30 | 0 | 4 | 3 | 5 | 5 | 5 | 0 | 2 | 4 | 5 | 5 | 5 |
|   | 10 | 0 | 0 | 0 | 5 | 3 | 3 | 0 | 0 | 0 | 5 | 5 | 5 |
| 14 | 30 | 0 | 2 | 3 | 5 | 5 | 5 | 0 | 3 | 3 | 5 | 5 | 5 |
|   | 10 | 0 | 2 | 4 | 5 | 5 | 5 | 0 | 4 | 5 | 5 | 5 | 5 |
| 15 | 30 | 0 | 5 | 5 | 5 | 5 | 5 | 0 | 5 | 5 | 5 | 5 | 5 |
|   | 10 | 0 | 1 | 5 | 5 | 5 | 4 | 0 | 1 | 3 | 5 | 5 | 5 |
| 16 | 30 | 0 | 5 | 5 | 5 | 5 | 5 | 0 | 5 | 5 | 5 | 5 | 5 |
|   | 10 | 0 | 0 | 0 | 0 | 2 | 3 | 0 | 0 | 0 | 0 | 2 | 5 |
| 17 | 30 | 0 | 0 | 0 | 0 | 2 | 3 | 0 | 0 | 0 | 0 | 4 | 5 |
|   | 50 | 0 | 2 | 2 | 0 | 5 | 5 | 0 | 0 | 4 | 2 | 5 | 5 |

Note:
The abbreviations each have the following significance:

Accordingly, the isoxazole derivatives (I) (Compound Nos. 1 to 16) hardly show herbicidal activity against *Triticum aestivum* but show an excellent and selective herbicidal activity against *Echinochloa crusgalli, Digitaria adscendens, Brassica campestris, Polygonum longisetum* and *Amaranthus retroflexus,* and their herbicidal activities are by far more potent than that of a commercially available herbicide, PCP-Na (Compound No. 17).

EXPERIMENT 2

Post-emergence test was effected by applying a suspension of 1-methyl-3-(5-t-butyl-3-isoxazolyl)urea to leaves and stalks of young plants under field conditions, and its herbicidal effects were examined. The following weeds could be killed by applying 10 to 30 g/are of the effective compound: *Eclipta prostrata, Senecio vulgaris, Polygonum chinense, Stellaria media, Malachium aquaticum, Mollugo pentaphylla, Rorippa islandica, Chenopodium album, Cerastium caespitosum, Portulaca oleracea, Galium spurium, Alopecurus aequalis, Euphorbia supina, Trigonotis peduncularis, Cyperus Iria, Setraria viridis, Sagina japonica, Stellaria uliginosa, Pinellia ternata, Rorippa indica, Mazus japnonicus, Gnaphalium multiceps, Oxalis Martiana, Lactuca stolonifera, Artemisia vulgalis, Calystegia japonica, Taraxacum platycarpum, Cirsium japonicum, Petasites japonicus, Pteridium aquilinum, Vandellia anagallis, Ludwigia prostrata, Potamogeton distinctus, Eleocharis acicularis.*

EXPERIMENT 3

Toxicity of 1-methyl-3-(5-t-butyl-3-isoxazolyl)urea to fishes was examined on Oryzias latipes and found to be very low in comparison with that of commercially available PCP-Na.

Presently-preferred and practical embodiments of the present invention are illustrated in the following examples.

EXAMPLE A 1,1-Dimethyl-3-(5-t-butyl-3-isoxazolyl)urea (10 parts by weight), Sorpol (Registered trademark; made by Toho Chemical Industry, Co., Ltd.) (10 parts by weight), cyclohexanone (20 parts by weight), and solvent naphtha (60 parts by weight) are admixed, whereby an emulsion is obtained.

EXAMPLE B

1-Butyl-3-(5-t-butyl-3-isoxazolyl)urea (50 parts by weight), calcium ligninsulfonate (3 parts by weight), Sorpol (Registered trademark: made by Toho Chemical Industry, Co., Ltd.) (3 parts by weight), and diatomaceous earth (44 parts by weight) are admixed and pulverized, whereby a wettable powder is obtained.

EXAMPLE C

1-Methyl-3-(5-i-propyl-3-isoxazolyl)urea (5 parts by weight), and clay (95 parts by weight) are admixed and pulverized, whereby a dust is obtained.

EXAMPLE D

1-Butyl-1-methyl-3-(5-t-butyl-3-isoxazolyl)urea (5 parts by weight), calcium ligninsulfonate (5 parts by weight), bentonite (30 parts by weight), and clay (60 parts by weight) are admixed, pulverized, mixed with water, kneaded, granulated, and dried, whereby granules are obtained.

What is claimed is:

1. A herbicidal composition comprising a herbicidal amount of a compound selected from the group consisting of 1-methyl-3-(5-i-propyl-3-isoxazolyl)urea, 1-methyl-3-(5-t-butyl-3-isoxazolyl)urea, 1,1-dimethyl-3-(5-t-butyl-3-isoxazolyl)urea, 1,3-dimethyl-3-(5-t-butyl-3-isoxazolyl)urea, 1,1,3-trimethyl-3-(5-t-butyl-3-isoxazolyl)urea, 1-methyl-1-butyl-3-(5-t-butyl-3-isoxazolyl)urea, 1-allyl-1-methyl-3-(5-t-butyl-3-isoxazolyl)urea, 1,1-dimethyl-3-(5-i-propyl-3-isoxazolyl)urea, 1-methoxy-1-methyl-3-(5-t-butyl-3-isoxazolyl)urea, 1-butylthio-1-methyl-3-(5-t-butyl-3-isoxazolyl)urea, 1-methyl-1-butyl-3-(5-i-propyl-3-isoxazolyl)urea and 1,3-dimethyl-3-(5-i-propyl-3-isoxazolyl)urea, in combination with a carrier therefor.

2. A composition according to claim 1, wherein the composition contains 1-methyl-3-(5-i-propyl-3-isoxazolyl)urea.

3. A composition according to claim 1, wherein the composition contains 1-methyl-3-(5-t-butyl-3-isoxazolyl)urea.

4. A composition according to claim 1, wherein the composition contains 1,1-dimethyl-3-(5-t-butyl-3-isoxazolyl)urea.

5. A composition according to claim 1, wherein the composition contains 1,3-dimethyl-3-(5-t-butyl-3-isoxazolyl)urea.

6. A composition according to claim 1, wherein the composition contains 1,1,3-trimethyl-3-(5-t-butyl-3-isoxazolyl)urea.

7. A composition according to claim 1, wherein the composition contains 1-methyl-1-butyl-3-(5-t-butyl-3-isoxazolyl)urea.

8. A composition according to claim 1, wherein the composition contains 1-allyl-1-methyl-3-(5-t-butyl-3-isoxazolyl)urea.

9. A composition according to claim 1, wherein the composition contains 1,1-dimethyl-3-(5-i-propyl-3-isoxazolyl)urea.

10. A composition according to claim 1, wherein the composition contains 1-methoxy-1-methyl-3-(5-t-butyl-3-isoxazolyl)urea.

11. A composition according to claim 1, wherein the composition contains 1-butylthio-1-methyl-3-(5-t-butyl-3-isoxazolyl)urea.

12. A composition according to claim 1, wherein the composition contains 1-methyl-1-butyl-3-(5-i-propyl-3-isoxazolyl)urea.

13. A composition according to claim 1, wherein the composition contains 1,3-dimethyl-3-(5-i-propyl-3-isoxazolyl)urea.

* * * * *

UNITED STATES PATENT OFFICE
CERTIFICATE OF CORRECTION

Patent No. 4,111,680      Dated September 5, 1978

Inventor(s) Hisajiro Yukinaga, Shinzaburo Sumimoto, Ichiro Ishizuka and Jitsuo Sugita It is certified that error appears in the above-identified patent and that said Letters Patent are hereby corrected as shown below:

In the Abstract, rewrite the first structural formula as follows:

-- 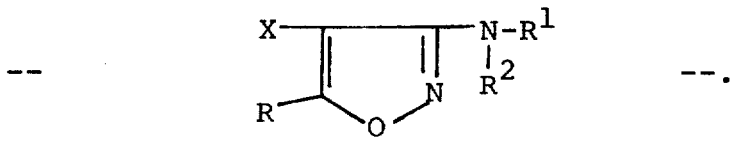 --.

Signed and Sealed this

Tenth Day of April 1979

[SEAL]

Attest:

RUTH C. MASON
Attesting Officer

DONALD W. BANNER
Commissioner of Patents and Trademarks

UNITED STATES PATENT OFFICE
CERTIFICATE OF CORRECTION

Patent No. 4,111,680   Dated September 5, 1978

Inventor(s) Hisajiro Yukinaga, Shinzaburo Sumimoto, Ichiro Ishizuka and Jitsuo Sugita It is certified that error appears in the above-identified patent and that said Letters Patent are hereby corrected as shown below:

In the first line of the Note immediately below Table 3 in column 8, change "ave" to --have--.

After "The abbreviations each have the following significance:" below Table 6 in column 15, insert the following:

-- A (Triticum aestivum), B (Echinochloa crusgalli), C (Digitaria adscendens), D (Brassica campestris), E (Polygonum logisetum), F (Amaranthus retroflexus). --

Signed and Sealed this

Eighteenth Day of December 1979

[SEAL]

Attest:

SIDNEY A. DIAMOND

Attesting Officer    Commissioner of Patents and Trademarks